United States Patent [19]

Wills et al.

[11] Patent Number: 4,519,100
[45] Date of Patent: May 28, 1985

[54] DISTAL LOCKING INTRAMEDULLARY NAIL

[75] Inventors: Robert P. Wills; Andrew F. Brooker, both of Baltimore, Md.

[73] Assignee: Orthopedic Equipment Co. Inc., Bourbon, Ind.

[21] Appl. No.: 430,411

[22] Filed: Sep. 30, 1982

[51] Int. Cl.³ .............................................. A61F 1/00
[52] U.S. Cl. .................... 3/1.9; 128/92 C; 128/92 BC; 128/92 BA
[58] Field of Search .......... 128/92 C, 92 BA, 92 CA, 128/92 B, 92 BB, 92 BC; 3/1.9

[56] References Cited

U.S. PATENT DOCUMENTS

| | | |
|---|---|---|
| 2,397,545 | 4/1946 | Hardinge . |
| 3,759,257 | 12/1973 | Fischer et al. . |
| 3,986,504 | 10/1976 | Avila .............. 128/92 BC |
| 4,091,806 | 5/1978 | Aginski . |
| 4,204,531 | 5/1980 | Aginski . |
| 4,227,518 | 10/1980 | Aginsky .......... 128/92 BC |
| 4,237,875 | 12/1980 | Termanini . |
| 4,275,717 | 6/1981 | Boleski . |

FOREIGN PATENT DOCUMENTS

| | | |
|---|---|---|
| 2117604 | 10/1972 | Fed. Rep. of Germany . |
| 2166339 | 1/1974 | Fed. Rep. of Germany . |
| 2701279 | 7/1977 | Fed. Rep. of Germany . |
| 587915 | 1/1959 | Italy .............. 128/92 BA |

Primary Examiner—Richard J. Apley
Assistant Examiner—D. J. Isabella
Attorney, Agent, or Firm—William D. Hall

[57] ABSTRACT

An improved intramedullary nailing device including a plurality of pivotal blades which rotate outward to engage the distal end of a fractured bone. Specifically, the blades are pivotally coupled to a connector member which translates longitudinally in either direction within an elongated sheath, translation of the connector member toward the front end of the sheath resulting in the outward rotation of the blades into the bone at its distal end. The bone engaging mechanism prevents rotation, angulation, and antero posterior translation with the device inserted lengthwise into the bone.

15 Claims, 4 Drawing Figures

FIG. 1
FIG. 4
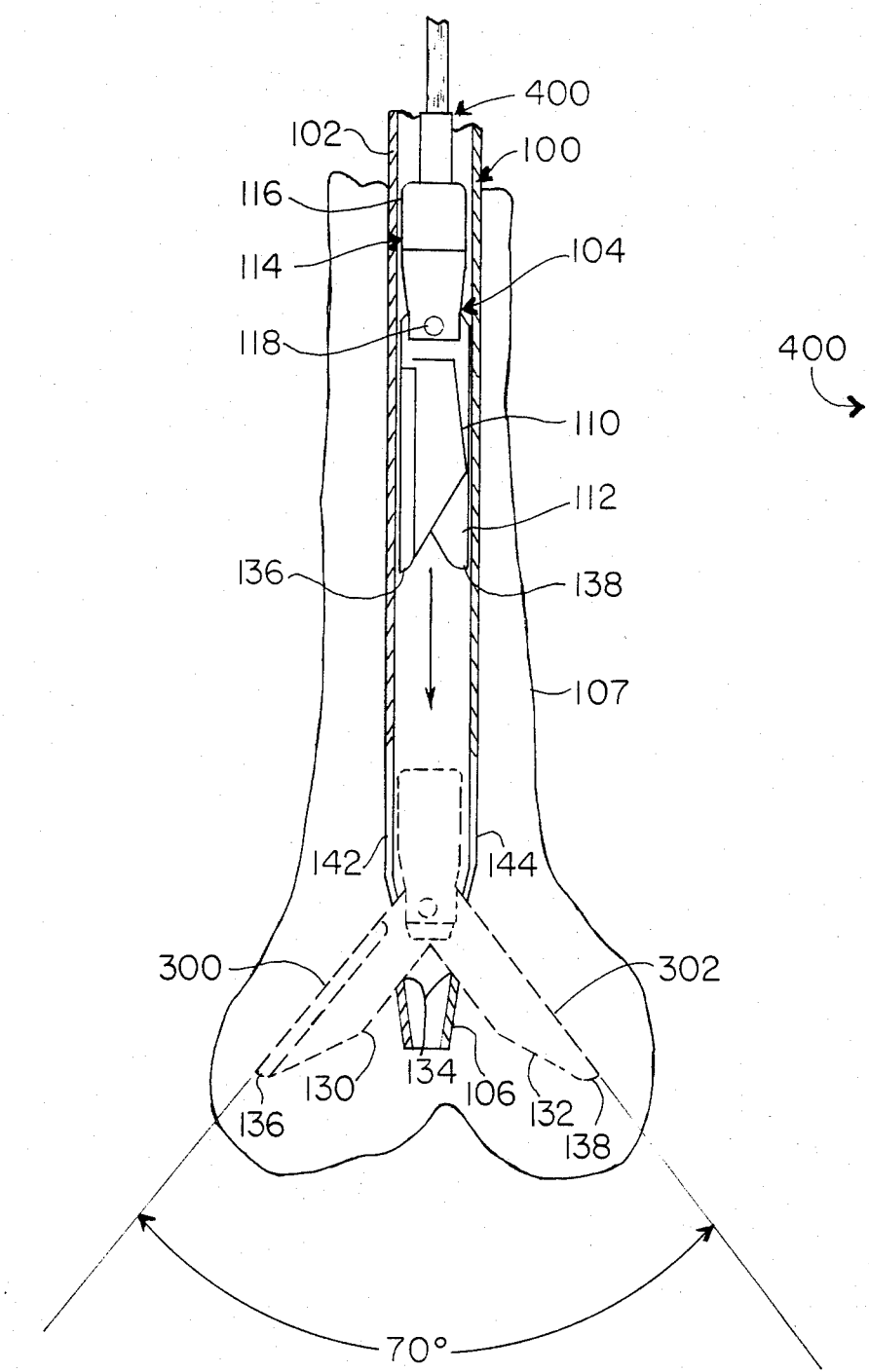
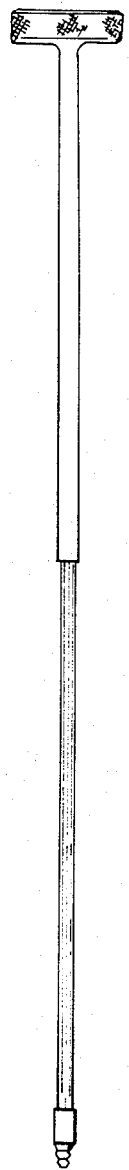

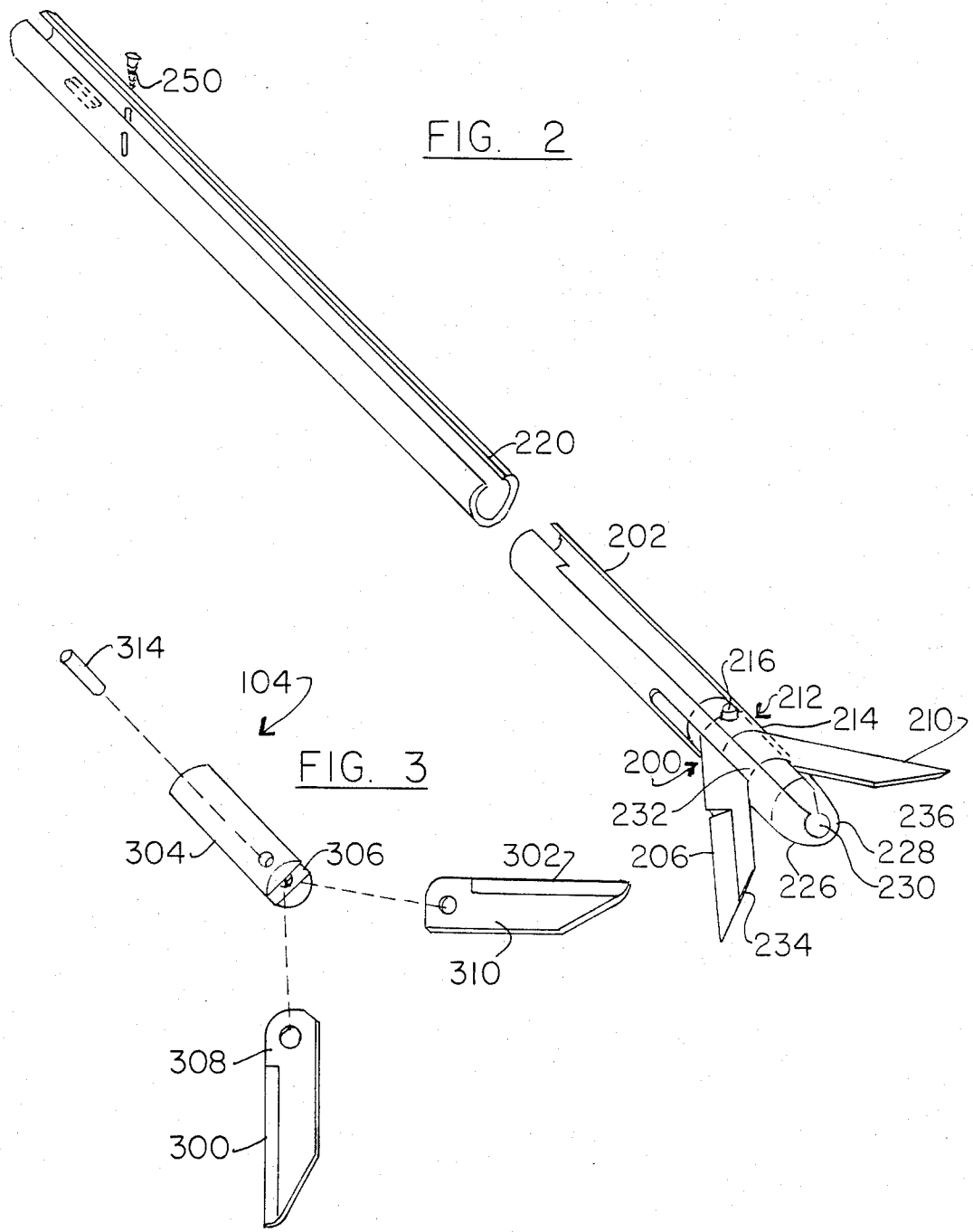

DISTAL LOCKING INTRAMEDULLARY NAIL

FIELD OF THE INVENTION

The present invention relates to an intramedullary nailing device.

BACKGROUND OF THE INVENTION

The nailing of fractured bones is taught in U.S. Pat. Nos. 2,397,545; 3,759,257; 3,986,504; 4,091,806; 4,204,531; 4,227,518; 4,237,875; 4,275,717 and German Pat. Nos. 2,117,604; 2,166,339; and 2,821,785.

The devices taught in these references do not rigidly hold a fracture distal to the femoral isthmus or permit weightbearing with dynamic compression. This is because such devices provide either (a) a fixed, rigid compression force or (b) a deploying mechanism which only guards against rotation. None of the reference teach the sliding upward of a distal locking device to allow ambulation and weightbearing which results when varying compressive forces are applied to the bone.

Further, none of the references disclose a distal lock mechanism comprising at least substantially flat blades which have outer sharp edges which engage a bone when the front end of each blades pivots outwardly about an axis orthogonal to the plane of each respective blade.

SUMMARY OF THE INVENTION

The present invention relates to an intramedullary nailing device capable of rigidly holding a fracture distal to the femoral isthmus. Specifically, the device includes at least two blades which scissor open, or outwardly, as the blades are advanced--within a hollow, elongated sheath--toward the distal end of a bone. The blades have relatively sharp edges which face outwardly and engage the bone as the blades are scissored open. The blades extend through respective longitudinal slots in the sheath, each slot having a width substantially equal to the width of the blade extending therethrough. Accordingly, it is an object of the invention to prevent rotation, angulation, or antero posterior translation with a distal locking intramedullary nail. In addition, a screw may be directed obliquely through the sheath and into a proximal portion of the bone. This results in better rotational fixation and greater compressional stability. Also, by directing the screw into the bone, proximal migration is prevented.

The longitudinal slots are also dimensioned to be longer than the length of the slot covered by a blade extending outwardly therethrough. This permits the blades to extend through the longitudinal slots at varying relative angles.

Further, it is also an object of the invention to provide an intramedullary nail having a distal locking mechanism wherein each bone-engaging blade, when scissored open, is longitudinally movable relative to the respective longitudinal slot through which each blade extends and to permit the distal locking mechanism to engage a bone under dynamic compression conditions.

The present invention includes a hollowed sheath which is essentially substitutable with a conventional nail. Accordingly, it is an object of the invention to provide a sheath to be inserted into a bone either with the distal locking mechanism included or, just conventionally, without the distal locking mechanism included.

BRIEF DESCRIPTION OF THE DRAWINGS

FIG. 1 is a cutaway view of one embodiment of the present invention with the blades shown in both (a) a retracted position and (b) a position with blades rotated outward to engage bone tissue.

FIG. 2 is a parts exposed, perspective view of a second embodiment of the present invention with blades extended outward.

FIG. 3 is an assembly drawing of the parts comprising the bone-engaging mechanism of the invention.

FIG. 4 is an illustration of a device used for inserting and extracting the bone-engaging mechanism.

DESCRIPTION OF THE INVENTION

In FIG. 1, an intramedullary nailing device 100 is shown including an elongated, hollow sheath 102 and a distal locking mechanism 104. The sheath 102 is shown to be substantially tubular along practically the entire length thereof, the front end 106 of the sheath 102 being tapered forward. The sheath 102 is, for the most part, the same as that of a standard conventional intramedullary nail. Accordingly, the sheath 102 can be driven into a bone 107 such as the femur, in standard fashion. That is, the sheath 102 is inserted with the front end 106 thereof being advanced toward the distal end of the bone 107.

The functioning of the distal locking mechanism 104 is also illustrated in FIG. 1. First, the distal locking mechanism 104 is shown in a retracted position (shown in solid line representation) with two blades 110 and 112 extending substantially longitudinally along and within the sheath 102. The blades 110 and 112 extend toward the front end 106 from a connector member 114. The connector member 114 is shown, preferably, as a cylindrical element 116 through which extends a pin 118. The blades 110 and 112 are each pivotally coupled to the connector member 114 at the pin 118. Also in FIG. 1, the connector member 114 is disposed to translate longitudinally within the sheath 102.

As the distal locking mechanism 104 is advanced, a predetermined point is reached at which the respective inner edge 130 and 132 of blades 110 and 112 strike a deflector element 134 which directs the front ends 136 and 138, respectively, of each blade 110 and 112 radially outward through longitudinal slots 142 and 144 in the sheath 102. The more the distal locking mechanism 104 is advanced toward the front end 106 of the sheath 102, the more the front ends 136 and 138 are rotated outwardly about the pin 118 through respective slots 142 and 144. In FIG. 1, the deflector element 134 is formed by the taper of the inner edge 130 and 132, respectively, of each blade 110 and 112 in cooperation with a taper of the sheath 102. As each blade 110 or 112 moves forward, the tapered inner edge thereof 130 or 132 strikes the forward border of slots 142 or 144, respectively. The blades 110 and 112 are thereby rotated outwardly into the bone as shown in the unretracted position (represented with dashed lines).

Referring to FIG. 2, a distal locking mechanism 200 is shown with a sheath 202. The distal locking mechanism 200, as in FIG. 1, includes blades 206 and 210 pivotally coupled to a connector member 212. The connector member 212 is formed of a cylinder 214 and a pin 216 therethrough. To guide the connector member 212 and the blades 206 and 210 coupled thereto along a longitudinal path, the pin 216 extends into a longitudinal track 220 defined along the entire length of the sheath 202.

Unlike the FIG. 1 embodiment, the invention as shown in FIG. 2 comprises a deflector element represented by a stub 226 disposed at the front end 228 of the sheath 202. The front part 230 of the stub 226 is conically shaped to fit into the tapered front end 228. The rear part 232 of the stub 226 is also conically shaped. The inner edges 234 and 236 of each blade 206 and 210 contact the rear part 232 of the stub 226 and slide therealong as the blades 206 and 210 are translated forward. As portions of the edges 234 and 236 closer to the pin 216 contact the rear part 232, the blades 206 and 210 are rotated outwardly further. A screw 250 is insertable obliquely through the sheath 202 and into the bone at its proximal end. This results in better rotational fixation and greater compressional stability. Also, by directing the screw 250 into the bone, proximal migration is prevented. The oblique angle is preferably approximately 30°.

As seen in FIG. 1, the blades 110 and 112 pivot about the same axis in opposite directions. When engaging the bone 107, the outer edges 300 and 302 thereof form an angle of, preferably, approximately 70°.

The exact structure of the distal locking mechanism 104 is shown in FIG. 3. Specifically, a cylinder 304 has a slit 306 at its forward end into which one end of each blade 308 or 310 fits. The outer edges 300 and 302 of each blade 308 and 310, respectively, are sharp along a length thereof. As each blade 308 or 310 rotates outwardly about a pin 314—which couples the blades 308 and 310 to the cylinder 304—the outer edges 300 and 302 are urged into the distal end of a bone (see FIG. 1).

To insert or remove the distal locking mechanisms in FIG. 1 (or FIG. 2), a device 400 shown in FIG. 4 is provided. The device 400 is also shown in FIG. 1 coupled to the cylindrical element 116. The device 400 is employed by tapping to translate the connector member 114 forward, resulting in the blades 110 and 112 scissoring outward. Withdrawing the device 400 results in the connector member 114 being moved rearward, together with the blades 110 and 112. The device 400 is selectively coupled to and decoupled from the connector member 114 by a screwing mechanism, as shown, or the like.

Examining FIGS. 1 and 2, it is noted that the longitudinal slots are dimensioned in width with respect to the width of the blade extending therethrough, in order to inhibit relative rotational movement. Further the length of each longitudinal slot is dimensioned to permit compression of the bone even when distally held by the present invention.

Finally, it is, of course, noted that the number of blades may be larger than two and that the connector member may be modified and still be within the contemplation of the invention. In any such embodiment, each blade is nonetheless pivoted about a respective axis, the front end of each such blade pivoting outward about its axis for bone engagement and inward for blade retraction as desired.

Other improvements, modifications and embodiments will become apparent to one of ordinary skill in the art upon review of this disclosure. Such improvements, modifications and embodiments are considered to be within the scope of this invention as defined by the following claims.

We claim:

1. A dynamic compression nail of intermedullary compression nailing, said nail comprising:

an elongated sheath having a front end and longitudinal slots proximate to said front end and at least partially circumferentially spaced therearound, means for fixedly attaching said sheath to the proximal end of the fractured bone, a conector member dimensioned to freely slide longitudinally within said sheath without rotation relative to said sheath, a plurality of blades pivotally coupled to said connector member, means for pivoting each blade outwarly to project through a respective one of said slots and to engage bone tissue at the distal end of the bone, wherein each slot has a greater longitudinal dimension than the width of the outwardly projecting blades thereby enabling said blades to translate longitudinally within said slot, and said blades are free to move axially with respect to said sheath within the length of said slots, and wherein said connector member and said pivoting means are arranged such that when said sheath is fixedly secured to said bone and said connector member is translated longitudinally towards said front end to engage said pivoting means, pivoting said blades outwardly through said slots and into said intermedullary bony tissue secures said nail across the fracture site and permits axial bone movement across the fracture site.

2. A device according to claim 1 wherein the blades extend at least substantially longitudinally within the sheath in a retracted position when the connector member is rearward of the predetermined point along the sheath, the blades being pivoted outward from the retracted position as the connector member is translated toward the front end of the sheath beyond a predetermined point.

3. A device according to claim 1 wherein the plurality of blades comprises two blades which pivot outwardly in opposite directions about the same pivot axis as the connector member is translated toward the front end of the sheath beyond a predetermined point.

4. An intramedullary device according to claim 1, wherein each blade has two ends, the first end being positioned distally relative to the second end, the distal end of each blade pivoting outwardly to project through the respective slot thereof and to engage tissue at the distal end of the bone.

5. An intrameduallary device according to claim 4, wherein each blade has an outwardly facing bevelled sharp edge; and wherein the bevelled sharp edge of each blade is driven into tissue at the distal end of the bone in response to said each blade being pivoted outwardly.

6. An intramedullary device according to claim 5 wherein each blade is substantially flat, the plane of each blade being orthogonal to the pivotal axis of said each blade.

7. An intramedullary device according to claim 6 further comprising:

means for pivoting each blade inwardly in response to translation of the connector member rearward away from front end of sheath.

8. An intramedullary device according to claim 7 wherein each blade has an inner edge along a length thereof; and wherein the means for pivoting the blade outwardly comprises a deflector element disposed at a predetermined point, the deflector element being positioned such that portions of the inner edge of each blade progressively closer to the pivotal axis of said each blade slide along the deflector element as the connector member translates toward the front end of the sheath, each blade pivoting increasingly outwardly as the inner edge portions progressively closer to the respective pivotal axis of said each blade contact and slide along the deflector element.

9. An intermedullary device according to claim 8 wherein the transverse dimension of each slot is slightly larger than the corresponding transverse blade dimension;

each blade projecting through the respective slot thereof into the bone, thereby preventing bone rotation while permitting dynamic compression of the bone.

10. An intramedullary device according to claim 9 wherein each blade has an inner edge which along a length thereof tapers toward the outer edge of said each blade at increasing distances from the pivotal axis of said each blade.

11. An intramedullary device according to claim 10 wherein the first end and the second end of each blade are aligned substantially longitudinally within the sheath when the connector member is positioned rearward of the predetermined point along the sheath by a given distance, the blades being pivoted outward as the connector member is translated toward the front end of the sheath beyond the predetermined point.

12. An intramedullary device according to claim 4 wherein the transverse dimension of each slot is slightly larger than the corresponding transverse blade dimension;

each blade projecting through the respective slot thereof into the bone thereby preventing bone rotation while permitting dynamic compression of the bone.

13. An intramedullary device according to claim 8 wherein the deflector element comprises a stub having a conical proximal end fixedly disposed within the sheath proximate to the front end of the sheath, portions of the inner edge of each blade progressively closer to the pivotal axis of said each blade sliding along the conical end of the stub as the connector member translates toward the front end of the sheath, each blade pivoting increasingly outwardly as the inner edge portions progressively closer to the respective pivotal axis of said each blade contact and slide along the conical end of the stub.

14. A device according to claim 10 wherein the plurality of blades comprises two blades which pivot outwardly in opposite directions about the same pivot axis as the connector member is translated toward the front end of the sheath beyond the predetermined point.

15. A device as in claim 1 wherein said means for fixedly attaching the sheath to the proximal end of the fractured bone includes a screw member insertable obliquely through the sheath and into the bone toward the proximal end thereof.

* * * * *